United States Patent [19]

Okamoto et al.

[11] 4,049,645
[45] Sept. 20, 1977

[54] N²-NAPHTHALENESULFONYL-L-ARGININE DERIVATIVES, AND THE PHARMACEUTICALLY ACCEPTABLE ACID ADDITION SALTS THEREOF

[75] Inventors: Shosuke Okamoto, Kobe; Ryoji Kikumoto; Kazuo Ohkubo; Shinji Tonomura, all of Tokyo; Yoshikuni Tamao; Tohru Tezuka, both of Yokohama; Akiko Hijikata, Kobe, all of Japan

[73] Assignees: Mitsubishi Chemical Industries Limited; Shosuke Okamoto, both of Tokyo, Japan

[21] Appl. No.: 671,568

[22] Filed: Mar. 29, 1976

Related U.S. Application Data

[63] Continuation-in-part of Ser. No. 622,390, Oct. 14, 1975, abandoned.

[30] Foreign Application Priority Data

| Nov. 8, 1974 | Japan | 49-128774 |
|---|---|---|
| Nov. 8, 1974 | Japan | 49-128775 |
| Nov. 29, 1974 | Japan | 49-136695 |
| Nov. 29, 1974 | Japan | 49-136697 |
| Feb. 25, 1975 | Japan | 50-23268 |
| Feb. 26, 1975 | Japan | 50-23635 |
| Mar. 5, 1975 | Japan | 50-26768 |
| Mar. 11, 1975 | Japan | 50-29357 |
| Mar. 11, 1975 | Japan | 50-29358 |

[51] Int. Cl.² .......... C07D 223/04; C07D 225/02; A61K 31/395; A61K 31/445; C07D 295/10; C07D 211/08; A61K 31/18; A61K 31/04

[52] U.S. Cl. .......... 260/239 B; 260/239 A; 260/239 BF; 260/268 BC; 260/288 R; 260/293.62; 260/306.7 R; 260/307 R; 260/307 H; 260/302 R; 260/465 D; 260/501.14; 260/326.11 R; 260/326.5 SF; 260/556 AR; 260/556 B; 424/250; 424/258; 424/262; 424/267; 424/270; 424/272; 424/274; 424/285; 424/309; 424/316; 424/321; 424/248.5; 544/158; 560/9

[58] Field of Search ........ 260/556 AR, 556 B, 239 A, 260/239 BF, 293.62, 465 D, 239 B

[56] References Cited

U.S. PATENT DOCUMENTS

| 3,622,615 | 11/1971 | Nicolaides et al. | 424/309 X |
| 3,867,447 | 2/1975 | Cherkofsky | 260/556 AR X |
| 3,978,045 | 8/1976 | Okamoto et al. | 260/556 AR X |

Primary Examiner—Daniel E. Wyman
Assistant Examiner—Thomas A. Waltz
Attorney, Agent, or Firm—Oblon, Fisher, Spivak, McClelland & Maier

[57] ABSTRACT

N²-naphthalenesulfonyl-L-arginine esters and amides having the formula

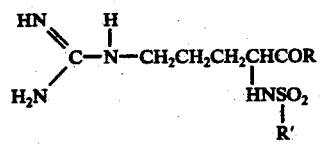

I or the acid addition salts thereof with a pharmaceutically acceptable acid, wherein R is

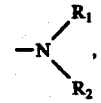

wherein $R_1$ and $R_2$ are members selected from the class consisting of hydrogen, alkyl, aryl, alkenyl and cycloalkyl, respectively containing not more than 10 carbon atoms, and aralykyl and cycloalkylalkyl, respectively containing not more than 15 carbon atoms; and R' is a member selected from the class consisting of 5,6,7,8-tetrahydro-1-naphthyl, 5,6,7,8-tetrahydro-2-naphthyl, 1-naphthyl, 2-naphthyl, 1-naphthyl substituted with halogen, nitro, cyano, hydroxy, alkyl containing not more than 10 carbon atoms, and 2-naphthyl substituted with halogen, nitro, cyano, hydroxy, alkyl containing ot more than 10 carbon atoms.

10 Claims, No Drawings

N²-NAPHTHALENESULFONYL-L-ARGININE DERIVATIVES, AND THE PHARMACEUTICALLY ACCEPTABLE ACID ADDITION SALTS THEREOF

RELATIONSHIP TO RELATED APPLICATIONS

This application is a continuation-in-part of application Ser. No. 622,390, filed Oct. 14, 1975, now abandoned.

BACKGROUND OF THE INVENTION

1. Field of the Invention

This invention relates to certain new and useful N²-naphthalenesulfonyl-L-arginine esters and amides, and the pharmaceutically acceptable acid addition salts thereof, which are of especial value in view of their outstanding antithrombotic properties.

2. Description of the Prior Art

In the past, there have been many attempts to obtain new and improved agents for the treatment of thrombosis. Of these, N²-(p-tolysulfonyl)-L-arginine esters are known to be effective in dissolving blood clots. (U.S. Pat. No. 3,622,615, patented Nov. 23, 1971). Also, N²-dansyl-1-arginine esters and amides are disclosed in U.S. patent application Ser. No. 496,939, now U.S. Pat. No. 3,978,045. A need continue to exist, however, for a highly specific inhibitor on thrombin for the control of thrombosis.

SUMMARY OF THE INVENTION

Accordingly, one object of the present invention is to provide a class of N²-naphthalenesulfony-L-arginine esters, amides and pharmaceutically acceptable acid addition salts thereof.

Another object of the present invention is to provide a class of N²-naphthalenesulfonyl-L-arginine esters, amides and pharmaceutically acceptable acid addition salts thereof which are useful in the diagnostic selective determination of thrombin in blood and in drug therapy as antithrombotic agents.

Briefly, these objects and other objects of the present invention as hereinafter will become more readily apparent can be attained by N²-naphthalenesulfonyl-L-arginine esters and amides of formula (I):

$$\begin{array}{c} HN \\ \diagdown \\ C-NH-(CH_2)_3CHCOR \\ \diagup \\ H_2N \end{array} \quad \begin{array}{c} \\ | \\ HN-SO_2 \\ | \\ R' \end{array} \tag{1}$$

or the acid addition salts thereof with a pharmaceutically acceptable acid, wherein R is selected from the class consisting of (I) alkoxy, alkenyloxy, halogenated alkoxy and cycloalkoxy, respectively containing not more than 10 carbon atoms, aralkyloxy of not more than 15 carbon atoms, and alkoxy of not more than 10 carbon atoms substituted with an alkoxy group of not more than 10 carbon atoms;

$$-N \begin{array}{c} R_1 \\ \diagdown \\ R_2 \end{array} \tag{2}$$

wherein $R_1$ and $R_2$ are members selected from the class consisting of hydrogen, alkyl, aryl, alkenyl and cycloalkyl, respectively containing not more than 10 carbon atoms, and aralkyl and cycloalkylalkyl, respectively containing not more than 15 carbon atoms, and substituted alkyl containing not more than 20 carbon atoms, said substituent being selected from the class consisting of alkoxy, alkoxycarbonyl, acyl, acyloxy, arylcarbomoyl and N,N-polymethylenecarbamoyl, respectively containing not more than 10 carbon atoms, and carboxy; and $$-N \bigcirc Z, \tag{3}$$

wherein Z is a divalent group containing up to 10 carbon atoms, which consists of more than one group selected from the class consisting of methylene —CH₂—, monosubstituted methylene $$\begin{array}{c} R_3 \\ | \\ -C- \\ | \\ H \end{array},$$

wherein $R_3$ is selected from the class consisting of alkyl, acyl, alkoxy, and alkoxycarbonyl, respectively containing not more than 10 carbon atoms, and carbamoyl, and disubstituted methylene $$\begin{array}{c} R_4 \\ | \\ -C- \\ | \\ R_5 \end{array},$$

wherein $R_4$ and $R_5$ are alkyl groups of not more than 10 carbon atoms, and which may further contain at least one member selected from the class consisting of oxy- O-, thio -S-, cycloalkylene of not more than 10 carbon atoms, imino $$\begin{array}{c} H \\ | \\ -N- \end{array},$$

alkyl-substituted imino $$\begin{array}{c} R_6 \\ | \\ -N- \end{array},$$

wherein $R_6$ is an alkyl group of not more than 10 carbon atoms, acyl-substituted imino $$\begin{array}{c} O=C-R_7 \\ | \\ -N- \end{array},$$

wherein $R_7$ is an alkyl group of not more than 10 carbon atoms, and phenylene $$-\underset{}{\bigcirc}-,$$

which may be arranged in any order and complete the

—NZ ring together with the said methylene, monosubstituted methylene or disubstituted methylene; and R' is a member selected from the class consisting of 5,6,7,8-tetrahydro-1-naphthyl, 5,6,7,8-tetrahydro-2-naphthyl, 1-naphthyl, 2-naphthyl, 1-naphthyl substituted with halogen, nitro, cyano, hydroxy, alkyl containing not more than 10 carbon atoms, and 2-naphthyl substituted with halogen, nitro, cyano, hydroxy, alkyl containing not more than 10 carbon atoms.

DETAILED DESCRIPTION OF THE PREFERRED EMBODIMENTS

Now the invention is explained in detail with respect to specific aspects thereof. In the above formula (I), examples of R are as follows:

1. In the case of ester derivatives, examples of R are an alkoxy group containing not more than 10 carbon atoms, e.g., methoxy, ethoxy, isopropoxy, propoxy, butoxy, tertbutoxy, pentyloxy, hexyloxy and the like; a cycloalkoxy group containing not more than 10 carbon atoms, e.g., cyclohexyloxy and the like; a halogenated alkoxy group containing not more than 10 carbon atoms, e.g., 2-chloroethoxy, 4-chlorobutoxy and the like; an alkoxy group of not more than 10 carbon atoms substituted with an alkoxy group of not more than 10 carbon atoms, e.g., 2-methoxyethoxy, 2-ethoxyethoxy and the like; an alkenyloxy group containing not more than 10 carbon atoms, e.g. allyloxy, 2-butenyloxy and the like; or an aralkyloxy group containing not more than 15 carbon atoms, e.g., benzyloxy, phenethyloxy, 1-phenylethoxy, 1-phenylpropoxy and the like. 2. In the case where

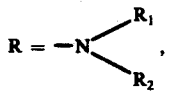

examples of $R_1$ and $R_2$ are indepently a hydrogen atom, an alkyl group containing not more than 10 carbon atoms, e.g., methyl, ethyl, propyl, isopropyl, butyl, isobutyl, pentyl, hexyl, heptyl and the like; an aryl group containing not more than 10 carbon atoms, e.g. phenyl, tolyl and the like; an aralkyl group containing not more than 15 carbon atoms, e.g., benzyl, phenethyl, 3-phenylpropyl and the like; a cycloalkyl group containing not more than 10 carbon atoms, e.g. cyclopropyl, cyclohexyl and the like; a cycloalkylalkyl group containing not more than 15 carbon atoms, e.g., cyclohexylmethyl, 3-cyclohexylpropyl and the like; an alkenyl group containing not more than 10 carbon atoms, e.g. allyl, crotyl, 2-hexenyl and the like; and an alkyl group containing not more than 10 carbon atoms substituted with an alkoxy group, an alkoxycarbonyl group, an acyl group, an acyloxy group, an arylcarbamoyl group or an N,N-polymethylenecarbamoyl group, respectively containing not more than 10 carbon atoms or a carboxy group, e.g., methoxyethyl, methoxypropyl, ethoxyethyl, ethoxycarbonylmethyl, 2-ethoxycarbonylethyl, 2methoxycarbonylethyl, 3-ethoxycarbonylpropyl, 2-acetylethyl, 2-acetoxyethyl, 2-phenylcarbamoylethyl, N,N-tetramethylenecarbamoylmethyl and the like. 3. In the case where

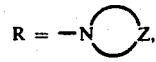

examples of R are a 1-polymethyleniminyl group, and those containing oxo or thio group, respectively containing not more than 10 carbon atoms, and a 1-polymethyleniminyl group containing not more than 10 carbon atoms substituted with an alkyl, acyl, alkoxy, or alkoxycarbonyl group, respectively containing not more than 10 carbon atoms, or carbamoyl, e.g., azetidinyl, 3-methoxy-1-azetidinyl, 3-ethoxy-1-azetidinyl, 1-pyrrolidinyl, 2-ethoxycarbonyl-1-pyrrolidinyl, 2-pyrrolidon-1-yl, piperidino, 4-piperidon-1-yl, 4-methylpiperidino, 4-ethylpiperidino, 4-propylpiperidino, 4-isopropylpiperidino, 2-methylpiperidino, 3-methylpiperidino, 2-ethoxycarbonyl-1-pyrrolidinyl, 4-methoxypiperidino, 4-oxopiperidino, 4-acetylpiperidino, 4-methoxycarbonylpiperidino, 4-carbamoylpiperidino, 1-hexamethyleniminyl, 1-octamethyleniminyl and the like; an oxazole and thiazole, such as 3-oxazolidinyl, 3-thiazolidinyl, and the like; an isoxazole and isothiazole, such as 2-isoxazolidinyl, 2-isothiazolidinyl, and the like; an oxazine, such as morpholino, 2,6-dimethylmorpholino, and an oxazine group represented by tetrahydro-1,n-oxazin-n-yl, such as tetrahydro-1,3-oxazin-4-yl and the like; a thiazine, such as tetrahydro-1,4-thiazin-4-yl and the like; 4-methyl-1-piperazinyl, 4-acetyl-1-piperazinyl, 1-piperazinyl, 2-isoindolinyl, 1-indolinyl, 1,2,3,4-teterahydro-2-isoquinolyl, 4-azabicyclo-[3.2.2]-non-4-yl, 1,2,3,4-tetrahydro-1-quinolyl and the like.

Examples of R' are 5,6,7,8 -tetrahydro-1or 2-naphthyl, 1-naphthyl, 2-naphthyl and 1- or 2-naphthyl substituted with halogen, e.g., chlorine or bromine, nitro, cyano, hydroxy; alkyl of not more than 10 carbon atoms, e.g., methyl, ethyl, propyl, isopropyl, butyl, tert-butyl and the like.

In the formula (I), R is preferably alkoxy of 1–8 carbon atoms, aralkyloxy of 7–9 carbon atoms, alkenyloxy of 3–6 carbon atoms, cyclohexyloxy, ω-alkoxyalkoxy of 2–6 carbon atoms, ω-chloroalkoxy of 2–6 carbon atoms, alkylamino of 1–9 carbon atoms, ω-alkoxyalkylamino of 2–6 carbon atoms, ω-alkoxycarbonylalkylamino of 2–8 carbon atoms, alkenylamino of 3–5 carbon atoms, cycloalkylamino of 3–6 carbon atoms, cyclohexylmethylamino, arylamino of 6–10 carbon atoms, aralkylamino of 7–10 carbon atoms, dialkylamino of 2–10 carbon atoms, N-alkyl-N-(ω-alkoxycarbonylalkyl)amino of 4–8 carbon atoms, N-alkyl-N-(ω-alkoxyalkyl)amino of 3–8 carbon atoms, N-alkyl-N-aralkylamino of 8–10 carbon atoms, N-alkyl-N-(ω-acylakyl)amino of 4–8 carbon atoms, N,N-polymethyleniminyl of 3–10 carbon atoms, N,N-polymethyleniminyl of 3–10 carbon atoms substituted with alkyl of 1–5 carbon atoms, alkoxy of 1–5 carbon atoms, alkoxycarbonyl of 2–5 carbon atoms, acyl of 2–5 carbon atoms, or carbamoyl; tetrahydro-1-,n-oxazin -n-yl, tetrahydro-1,n-thiazin-n-yl, wherein n is an integer of 2, 3 or 4, tetrahydro-1,n-oxazin-n-yl, wherein n is an integer of 2, 3 or 4 and which is substituted with one or two alkyl groups of 1–5 carbon atoms; 2-isoindolinyl, 1-piperazinyl, 1-piperazinyl substituted with alkyl of 1–5 carbon atoms or acyl of 2–5 carbon atoms, 4-arkyl-1-piperzinyl of 5–8 carbon atoms, or 4-azabicyclo[3.2.2]-non-4-yl.

R' is preferably 1-naphthyl, 2-naphthyl, 5,6,7,8-tetrahydro-1-naphthyl, 5,6,7,8-tetrahydro-2-naphthyl, 6-methyl-2-naphthyl, 7-methyl-1-naphthyl, 7-methyl-2- naphthyl, 6-ethyl-2-naphthyl, or 5-(N,N-diethylamino)-1-naphthyl.

Typical compounds of this invention include:

1. In the case of the ester derivatives:
   N²-(6-ethyl-2-naphthalenesulfonyl)-L-arginine butyl ester, N²-(6-ethyl-2-naphthalenesulfonyl)-L-arginine crotyl ester;

2. In the case of the amide derivatives, wherein

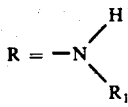 (i)

(R₁ is not hydrogen):
   N²-(5,6,7,8-tetrahydro-1-naphthalenesulfonyl)-N-benzyl-L-argininamide;

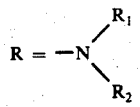 (ii)

(neither R₁ nor R₂ is hydrogen):
   N²=(5-methoxy-1-naphthalenesulfonyl)-N-melthyl-N-butyl-L-argininamide, N²-(5,6,7,8-tetrahydro-1-naphthalenesulfonyl)-N-methyl-N-benzyl-L-argininamide;

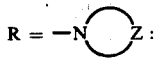 (iii)

4-[N²-(5,6,7,8-tetrahydro-2-naphthalenesulfonyl)-L-arginyl]morpholine, 4-ethyl-[N²-(5,6,7,8-tetrahydro-1-naphthalenesulfonyl)-L-arginyl]piperidine, 4-methyl-[N²-(5,6,7,8-tetrahydro-1-naphthalenesulfonyl)-L-arginyl]piperidine, 4-ethyl-1-[N²-(5,6,7,8-tetrahydro-2-naphthalenesulfonyl)-L-arginyl]piperidine, 4-ethyl-1-[N²-(1 -naphthalenesulfonyl)-L-arginyl]piperdine, 4-methyl -1-[N²-(1-naphthalenesulfonyl)-L-arginyl]piperidine, 4-ethyl-1[N²-(2-naphthalenesulfonyl)-L-arginyl]piperedine, 4-methyl-1-[N²-(2-naphthalenesulfonyl)-L-arginyl]piperidine, 4-ethyl-1-[N²-(6-methyl-2-naphthalenesulfonyl)-L-arginyl]piperdine, 4-ethyl-1-[N²-(7-methyl-2-naphthalenesulfonyl)-L-arginyl]piperidine, 4-ethyl-1-[N²-8 6-dimethylamino-2-naphthalenesulfonyl)-L-arginyl]piperidine, 4-methoxyl-[N²-(7-methoxy-2-naphthalenesulfonyl)-L-arginyl]-piperidine, 4-methoxycarbonyl-1[N²-(6-methoxy-2-naphthalenesulfonyl)-L-arginyl]piperidine, N²-[5,6,7,8-tetrahydro-1naphthalene-sulfonyl]-N,N-heptamethyleniminyl-L-argininamide, 2-[N²-(1-naphthalenesulfonyl)-L-arginyl]isoindoline.

These typical compounds are highly potent in their antithrombotic acitivity.

For the preparation of the compounds of this invention, various methods can be employed depending upon the particular starting materials and/or intermediates involved. Successful preparation of these compounds is possible by way of several synthetic routes which are outlined below.

1. Preparation of N²-naphthalenesulfonyl-L-arginine esters a. Esterfication of an N²-naphthalenesulfonyl-1-arginine N²-naphthalenesulfonyl-L-arginines, which are the starting materials for the preparation of N²-naphthalenesulfonyl-L-arginine esters, are most generally obtained by reacting L-arginine and a naphthalenesulfonyl halide, in the presence of a base.

The naphthalenesulfonyl halides to be used are represented by the general formula R'—SO₂X, wherein R' is the same as in formula (I) and X is a halogen atom such as chlorine or bromine. Usually a naphthalenesulfonyl chloride is preferred.

However, N²-naphthalenesulfonyl-L-arginines may also be obtained by reacting ornithine, the ω-position of which is protected, with a naphthalenesulfonyl halide in the presence of a base, removing the protective group at the ω-position of the product, and thereafter guanidylating the N²-naphthalenesulfonylornithine by conventional procedures. N²-naphthalenesulfonyl-L-arginine esters or acid addition salts thereof are prepared by esterifying the above-mentioned N²-naphthalenesulfonyl-L-arginine in accordance with the processes explained below.

i. Esterification by heating an N²-naphthalene sulfonyl-L-arginine and an alcohol.

The reaction rate is low in this method, which is therefore conducted under high pressure at an elevated temperature. Care must be excercised, since N²-naphthalenesulfonyl-L-arginines are easily decomposed at high temperatues.

ii. Esterification of an N²-naphthalenesulfonyl-L-arginine with an alcohol in the presence of an esterification catalyst.

Suitable esterification catalysts include hydrogen halides, such as hydrogen chloride, hydrogen bromide or the like; mineral acids such as sulfuric acid, nitric acid, phosphoric acid, or the like; organic acids, such as toluene sulfonic acid, benzenessulfonic acid, methanesulfonic acid, trifluoromethanesulfonic acid, trifluoroacetic acid, cationic ion exchange resins or the like; and Lewis acids, such as boron trifluoride, aluminum chloride, or the like. Strong acids are especially suitable.

A strong acid esterification catalyst adds to an N²-naphthalenesulfonyl-L-arginine ester to form an acid addition salt thereof. Normally, 1 equivalent of the acid add to 1 equivalent of the N²-naphthalenesulfonyl-L-arginine ester, and therefore, 1 equivalent or more of the esterfication catalyst are preferably used for each 1 equivalent of the N²-naphthalenesulfonyl-L-arginine.

Suitable alcohols for the above-mentioned esterfication include primary, secondary, and tertiary alkyl alcohols containing up to 10 carbon atoms, such as methanol, ethanol, propanol, isopropyl, alcohol, butanol, tert-butyl alcohol, pentanol, hexanol, 2-ethylhexanol; aralykyl alcohols containing up to 15 carbon atoms, such as benzyl alcohol, phenethyl alcohol, 1-phenylethanol, 1-phenyl-1-propanol, or the like; alkenyl alcohols containing up to 10 carbon atoms, such as allyl alcohol, crotyl alcohol, methyl vinyl carbinol, or the like; cycloalkyl alcohols containing up to 10 carbon atoms, such as cyclohexanol, cyclopentanol, or the like; and alkyl alcohols containing up to 10 carbon atoms substituted with an alkoxy group of up to 10 carbon atoms or a halogen, such as 3-chloro-1-propanol, 2-chloro-1-propanol, 1-chloro-2-propanol, 2-fluoro-1-ethanol, 2-chloro-1-ethanol, 4-chloro-1-butanol, 2-methoxyethanol, 3-ethoxypropanol, or the like.

An N²-naphthalenesulfonyl-L-arginine reacts with an equimolar amount of an alcohol. However, at least 5 moles of the alcohol per mole of the N²-naphthalenesulfonyl-L-arginine are preferably employed to enhance the reaction rate.

The esterification reaction can be carried out in a reaction-inert solvent, such as an aromatic hydrocarbon, e.g., benzene, toluene, xylene, or the like; a chlorinated hydrocarbon, e.g., carbon tetrachloride, chloroform, dichloromethane, or the like; a hydrocarbon solvent, e.g., hexane, cyclohexane, or the like; an ether, e.g, dioxane, tetrahydrofuran, or the like; or a mixture of these compounds. Especially preferred solvents include benzene, toluene, xylene, cyclohexane, carbon tetrachloride and dichloromethane, which form azeotropic mixtures with water, and are therefore advantageous for the esterification reaction, since water formed during the reaction can be easily removed, and the reaction can be carried out advantageously at equilibrium.

The reaction temperature varies with the alcohol and the catalyst to be employed. Generally, the temperature ranges from 0° C to the boiling point of the alcohol or solvent. The reaction time varies widely with the alcohol and catalyst employed and normally ranges from 10 minutes to 15 hours.

After the reaction is completed, the alcohol and/or solvent is distilled off, and an $N^2$-naphthalenesulfonyl-L-arginine ester or an acid addition salt thereof is obtained. Normally, 1equivalent of the acid esterification catalyst adds to the $N^2$-naphthalenesulfonyl-L-arginine ester.

The acid addition salt can be easily converted to the corresponding $N^2$-naphthalenesulfonyl-L-arginine ester by adjusting the pH of the medium.

The $N^2$-naphthalenesulfonyl-L-arginine esters and the acid addition salts thereof can be purified by recrystallization from the combination of solvents, such as ethyl ether, alcohols, acetone or the like, or reprecipitating by addition of ether to an alcohol solution of the compounds.

iii. Esterification of an $N^2$-naphthalenesulfonyl-L-arginine with an alcohol and a thionyl halide Suitable thionyl halides include thionyl chloride and thionyl bromide. The $N^2$-naphthalenesulfonyl-L-arginine reacts with an equimolar amount of the thionyl halide. However, it is desirable to employ at least 2 moles of the thionyl halide per one mole of the $N^2$-naphthalenesulfonyl-L-arginine in order to drive the reaction to completion. During the reaction, the thionyl halide decomposes to a hydrogen halide and $SO_2$, and the formed hydrogen halide adds to the $N^2$-naphthalenesulfonyl-L-arginine ester to generally form a halogeno acid salt of the $N^2$-naphthalenesulfonyl-L-arginine ester.

The other reaction conditions and the procedures for separation and purification of the product are the same as in process (ii) (esterification with an esterification catalyst).

(iV). Preparation of an $N^2$-naphthalenesulfonyl-L-arginine methyl ester

An $N^2$-naphthalenesulfonyl-L-arginine methyl ester can be prepared by the reaction of an $N^2$-naphthalenesulfonyl-L-arginine with diazomethane; reaction of an $N^2$-naphthalenesulfonyl-L-arginine with dimethyl sulfite and tosylsulfonic acid; and reaction of an $N^2$-naphthalenesulfonyl-L-arginine with dimethyl sulfate.

v. Reaction of an alkali metal salt of an $N^2$-naphthalenesulfonyl-L-arginine with an alkyl halide.

Alkyl esters of an $N^2$-naphthalenesulfonyl-L-arginine can be prepared by reacting an alkali metal salt of an $N^2$-naphthalenesulfonyl-L-arginine and an alkyl halide in a polar solvent.

In addition, an $N^2$-naphthalenesulfonyl-L-arginine may be esterified by other processes, but processes (ii) and (iii) are generally used.

b. Reaction of an L-arginine ester with a naphthalenesulfonyl halide

L-arginine esters or acid addition salts thereof, which are used as the starting materials of $N^2$-naphthalenesulfonyl-L-arginine esters or acid addition salts thereof, are most generally obtained by reacting L-arginine with an alcohol in the presence of an acid catalyst. When the esterification is carried out in the presence of an acid catalyst, an acid addition salt of an L-arginine ester is usually obtained.

The naphthalenesulfonyl halides usable for this process has been defined hereinbefore.

The reaction of an L-arginine ester or an acid addition salt thereof with a naphthalenesulfonyl halide is normally carried out in the presence of a base. The base captures the hydrogen halide formed during the reaction and enhances the reaction rate.

Suitable bases include organic bases, such as triethylamine, pyridine, or the like; and common inorganic bases such as sodium hydroxide, potassium hydroxide, potassium carbonate, or the like. The inorganic bases are usually used as an aqueous solution.

The base is normally used in an amount at least equivalent to the L-arginine ester. When an acid addition salt of an L-arginine ester is used as the starting material, an excess of the base sufficient to convert the L-arginine ester acid addition salt to the L-arginine ester is desirably used in addition to the amount to be used as the catalyst.

The naphthalenesulfonyl halide reacts with an equimolar amount of an L-arginine ester or an acid addition salt thereof. The reaction of an L-arginine ester or an acid addition salt thereof and a naphthalenesulfonyl halide is usually carried out in a solvent. Suitable solvent include water; chlorinated solvents, such as dichloromethane, chloroform, carbon tetrachloride, and the like; aromatic hydrocarbons, such as benzene, toluene, xylene and the like; ethers such as ethyl ether, tetrahydrofuran, tetrahydropyran and the like; ketones such as acetone, methyl ethyl ketone, cyclohexanone and the like; basic solvents, such as dimethylacetamide, dimethylformamide, tetramethylurea, N-methylpyrrolidone, pyridine, quinoline, and the like; or a mixture of two or more of these solvents. A basic solvent acts as an acid acceptor, and therefore the addition of the base is unnecessary when such solvent is used.

The reaction temperature is dependent on the arginine esters and bases to be employed, but is generally between 0° C and the boiling temperature of the solvent employed.

The reaction time varies with the arginine ester and is usually between 10 minutes and 15 hours.

After the reaction is completed, the produced salt is washed away with water, the solvent is removed by distillation, and the obtained product is washed with water and/or the solvent. To the thus obtained $N^2$-naphthalenesulfonyl-L-arginine ester, an acid (e.g., hydrochloric acid, p-toluenesulfonic acid, or the like) is added, and the formed acid addition salt of the $N^2$-naphthalenesulfonyl-L-arginine ester is isolated.

2. Preparation of N²-naphthalenesulfonyl-L-argininamides a. Reaction of an N²-naphthalenesulfonyl-L-argine ester with a primary amine Suitable N²-naphthalenesulfonyl-L-arginine esters or the acid addition salts thereof include the methyl ester, ethyl ester, isopropyl ester and the like or the hydrochlorides thereof. Suitable amines include primary amines, such as an alkylamine containing not more than 10 carbon atoms, e.g., methylamine, ethylamine, propylamine, isopropylamine, butylamine, hexlamine, heptylamine and the like; an aralkylamine containing not more than 15 carbon atoms, e.g., phenethylamine and the like; a cycloalklamine containing not more than 10 carbon atoms, e.g., cyclopropylamine, cyclobutylamine, cyclopentylamine, cyclohexylamine, cyclooctylamine, 4-methylcyclohexylamine, and the like; an alkylamine containing not more than 10 carbon atoms substituted with an alkoxy group containing not more than 10 carbon atoms, e.g., 2-methoxy, ethylamine, 2-ethoxyethylamine, 3-methoxypropylamine, 3-methoxybutylamine, 3-methoxypentylamine and the like; a cycloalkylalkylamine containing not more than 15 carbon atoms, e.g., cyclohexylmethylamine, 2-cyclohexylethylamine, cyclobutylmethylamine, 3-cyclopentylbutylamine and the like, and an alkenylamine containing not more than 10 carbon atoms, e.g., allylamine, crotylamine, 3-butenylamine and the like.

The amine is preferably used in an amount equivalent to or greater than the N²-naphthalenesulfonyl-L-arginine ester. The amine is preferably used in excess in order to enhance the reaction rate and to carry out the reaction advantageously at equilibrium. The amine is usually used in an amount 2 to 10 times the molar quantity of the N²-naphthalenesulfonyl-L-arginine ester. When an acid addition salt of an N²-naphthalenesulfonyl-L-arginine ester is used, the amine is usually converted to an acid addition salt. Therefore, it is necessary to use an amine corresponding to the acid addition salt of the amine to be formed in excess.

A basic compound may be used as a catalyst. Specifically, an alkali metal alkoxide, such as sodium methoxide or a tertiary amine, such as pyridine or the like are preferable. When these catalysts are used, the reaction rate is enhanced and therefore the amine can be used in a lesser amount and milder reaction conditions are thus possible.

If the amine is used in large excess, N²-naphthalenesulfonyl-L-arginine esters or acid addition salts thereof will dissolve in the amine, and therefore the reaction will proceed without a solvent. However, solvents, such as alcohols, e.g., methanol, ethanol, butanol and the like; ethers, e.g., ethyl ether, tetrahydrofuran, tetrahydropyran, dioxane and the like; hydrocarbons, e.g., benzene, toluene, cyclohexane and the like; halogenated hydrocarbons, e.g., carbon tetrachloride, chloroform, dichloromethane and the like; and water can be used.

The reaction is usually carried out by mixing an N²-naphthalenesulfonyl-L-arginine ester or an acid addition salt thereof with an excess amount of an amine, the resulting homogeneous solution is allowed to stand at room temperature. However, the reaction mixture can be heated to a temperature up to the boiling temperature of the amine or solvent to enhance the reaction rate.

The reaction time is dependent on the basicity and amount of the amine employed, among other factors, but usually ranges from several hours to several days.

After the reaction is completed, the product is collected by filtration, washed with water, and purified by recrystallization from a suitable solvent, e.g., aqueous methanol, or the like. If solid product does not form, the excess amine and/or the solvent is removed by distillation, and the residue is washed and purified by recrystallization from a suitable solvent.

b. Reaction of an L-argininamide with a naphthalenesulfonyl halide

An L-argininamide or an acid addition salt thereof can be obtained by protecting the guanidino group and α-amino group of the arginine via nitration, acetylation, formylation, phthaloylation, trifluoroacetylation, p-methoxybenzyloxycarbonylation, benzoylation, benzyloxycarbonylation, t-butoxycarbonylation or tritylation, then condensing the obtained arginine derivative with an amine by a conventional method such as the acid halide method, azide method, mixed anhydride method, activated ester method, carbodiimide method, or the like, and thereafter removing the protective group by the known method. The suitable naphthalenesulfonyl halides have already been explained hereinbefore with respect to the preparation of N²-naphthalenesulfonyl-L-arginines.

The reaction of an L-argininamide or an acid addition salt thereof and a naphthalenesulfonyl halide is usually carried out in the presence of a base. The basic compound captures the hydrogen halide which is formed during the reaction, and thus promotes the reaction.

Suitable bases include organic bases such as triethylamine, pyridine and the like; or inorganic bases, such as sodium hydroxide, potassium hydroxide, potassium carbonate and the like. Inorganic bases are usually used as an aqueous solution.

The base is used in excess of the amount equivalent to the L-argininamide. When an acid addition salt of an L-argininimide is used, a base is preferably used in an amount sufficient to convert the acid addition salt of the L-argininamide to the free L-argininamide in addition to the amount of the base to be used as the catalyst.

A naphthalenesulfonyl halide is usually reacted with an equimolar amount of an L-argininamide or an acid addition salt thereof in a solvent. Suitable solvents include water; chlorinated hydrocarbons such as dichloromethane, chloroform, carbon tetrachloride and the like; aromatic hydrocarbons, such as benzene, toluene, xylene and the like; ethers, such as ethyl ether, tetrahydrofuran, dioxane, tetrahydropyran and the like; ketones, such as acetone, methyl ethyl ketone, cyclohexanone and the like; basic solvents, such as dimethylacetamide, dimethylformamide, tetramethylurea, N-methylpurrolidone, pyridine, quinoline and the like; or a mixture of two or more of these solvents. A basic solvent acts as an acid acceptor, and therefore further addition of the base is not required in these instances.

The reaction temperature is dependent on the species of the L-argininamide and base, but usually between 0° C and the boiling temperature of the solvent. The reaction time varies with the L-argininamide and is usually between 10 minutes and 15 hours.

After the reaction is completed, the formed salt is removed by washing with water, solvent is removed by distillation, and the obtained product is washed with water and/or the solvent, and the N²-naphthalenesulfonyl-L-argininamide is obtained. The thus obtained N²-naphthalenesulfonyl-L-argininamide can be isolated in the form of an acid addition salt thereof by the addition of an acid (e.g., hydrochloric acid, p-toluenesulfonic acid, and the like).

c. Elimination of the $N^G$-substituent from an $N^G$-substituted-N²-naphthalenesulfonyl-L-argininamide having the formula (II)

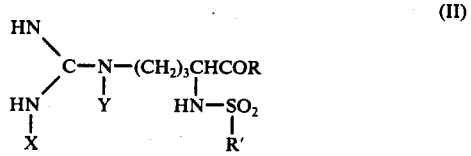

An N²-naphthalenesulfonyl-L-argininamide is prepared by eliminating the $N^G$-substituent from an $N^G$-substituted-N²-naphthalenesulfonyl-L-argininamide having the above formula (II) by means of acidolysis or hydrogenolysis. In the formula (II), R and R' are the same as the formula (I), X and Y are selected from hydrogen and protective groups for the guanidino group, and at least one of them is a protective group. Suitable protective groups include nitro, tosyl, trityl, or an oxycarbonyl, such as benzyloxycarbonyl, p-nitrobenzyloxycarbonyl, p-methoxybenzyloxycarbonyl, tertbutoxycarbonyl and the like.

The $N^G$-substituted-N²-naphthalenesulfonyl-L-argininamides as represented by general formula (II) or acid addition salts thereof can be obtained by condensing an $N^G$-substituted N²-substituted arginine (usually the N²-substituent is a protective group for the amino group, such as benzyloxycarbonyl, t-butoxycarbonyl, or the like) and an amine via the azide method, mixed anhydride method, activated ester method, carbodiimido method or the like, selectively removing only the N²-substituent by means of catalytic hydrogenolysis or acidolysis, and reacting the thus obtained $N^G$-substituted-L-argininamide or an acid addition salt thereof with a naphthalenesulfonyl halide, as defined in the above, in the presence of a base in a solvent. Suitable bases include organic bases, such as triethylamine, pyridine and the like; or inorganic bases, such as sodium hydroxide, potassium hydroxide, potassium carbonate, sodium hydrogen carbonate and the like. Inorganic bases are normally used as an aqueous solution.

The base is preferably used in an amount not less than the amount equivalent to the $N^G$-substituted-L-argininamide. When an acid addition salt of an $N^G$-substituted-L-argininamide is used, the base is preferably used in an amount sufficient to neutralize the acid addition salt in addition to the amount to be used as the catalyst. The naphthalenesulfonyl halide is normally used in an equimolar amount to the $N^G$-substituted-L-argininamide.

Suitable solvents include water; chlorinated solvents, such as dichloromethane, chloroform, carbon tetrachloride and the like; aromatic hydrocarbons, such as benzene, toluene, xylene and the like; ether, such as ethyl ether, tetrahydrofuran, dioxane and the like; ketones, such as acetone, methyl ethyl ketone, cyclohexanone, and the like; basic solvents such as dimethylacetamide, dimethylformamide, tetramethylurea, N-methylpyrrolidone, pyridine, quinoline, and the like; or a mixture of two or more of the abovementioned solvents. A basic solvent acts as an acid acceptor, and therefore further addition of the base is not required in these instances.

The reaction temperature is dependent on the $N^G$-substituted-L-argininamide and base, but usually ranges from $-10°$ C to the boiling temperature of the solvent.

The reaction time varies with the species of the $N^G$-substituted-L-argininamide and base, and the reaction temperature, and is usually from 5 minutes to 24 hours.

After the reaction is completed, the solvent and base are distilled off, the formed salt is removed by washing with water, and the $N^G$-substituted-N²-naphthalenesulfonyl-L-argininamide is purified by recrystallizing or reprecipitating from a suitable solvent. The reaction product may also be separated and purified by means of chromatography. Suitable elutants include chlorinated solvents, such as chloroform, dichloromethane and the like; a chlorinated solvent containing alcohol and the like.

As explained above, the N²-naphthalenesulfonyl-L-argininamide represented by general formula (II) or an acid addition salt thereof is obtained from the $N^G$-substituted-N²-naphthalenesuflonyl-L-argininamide bu removing the $N^G$-substituent, which is a protective group for the guanidino group of the amide, via hydrogenolysis or acidolysis.

Suitable acids for the acidolysis include hydrogen halides, such as hydrogen chloride, hydrogen bromide, hydrogen fluoride; and organic acids, such as trifluoroacetic acid, trifluoromethanesulfonic acid, formic acid, acetic acid, and the like.

The acidolysis is preferably carried out by treating the $N^G$-substituted-N²-naphthalenesulfonyl-L-argininamide or the acid addition salt thereof with any of the above-mentioned acids without a solvent or in a solvent, such as an alcohol, e.g., methanol, ethanol and the like; an ether, e.g., tetrahydrofuran, dioxane, anisole and the like; an organic acid, e.g., acetic acid and the like; or an ester, e.g., ethyl acetate and the like, at a temperature between $-10°$ C and $+100°$ C, preferably at room temperature. The time required for the acidolysis varies with the acid and solvent, the protective $N^G$-substituent, and the temperature of treatment, and is from 30 minutes to 24 hours.

After the decomposition is completed, the N²-naphthalenesulfonyl-L-argininamide or an acid addition salt thereof is obtained by removing the solvent and the excess acid or adding to the reaction mixture an inert solvent, such as ethyl ether, petroleum ether, a hydrocarbon solvent, or the like so as to form a precipitate and collecting the precipitate. An excess of the acid is usually used, and therefore the N²-naphthalenesulfonyl-L-argininamide which is obtained by removing the protective group is in the form of an acid addition salt. This salt can be easily converted to a free amide by neutralization.

Hydrogenolysis can be carried out according to any of the general procedures of reductive hydrogenation, although catalytic hydrogenation is most advantageous. Catalytic hydrogenation is carried out in the presence of a hydrogen-activating catalyst in a hydrogen atmosphere. Suitable hydrogen-activating catalyst include Raney nickel, palladium, platinum and the like. Suitable solvents include alcohols, such as methanol, ethanol and the like; ethers, such as dioxane, tetrahydrofuran and the like; organic acids, such as acetic acid, propionic acid and the like; or a mixture of two or more of the above-mentioned solvents.

The reaction temperature is dependent on the protective group for the guanidino group and the activity of the employed catalyst, and is usually between 0° C and the boiling temperature of the solvent. The hydrogen pressure is dependent on the reaction temperature and activity of the catalyst. Atmospheric pressure is sufficient for the reaction, although higher pressure may be employed. The reaction time is dependent on the activity of the catalyst, the reaction temperature, the hydrogen pressure and the like and is usually from 2 hours to 120 hours.

After the hydrogenolysis is finished, the catalyst is removed by filtration, the solvent is removed by distillation, and the $N^2$-naphthalenesulfonyl-L-argininamide or the acid addition salt thereof is obtained. The acid addition salt is easily converted to the free $N^2$-naphthalenesulfonyl-L-argininamide by neutralization.

The thus obtained $N^2$-naphthalenesulfonyl-L-argininamide or the acid addition salt thereof is purified by recrystallization from a solvent which is a mixture of two or more of the following: water, ethyl ether, alcohols, acetone, or the like, or by reprecipitation by addition of ethyl ether to an alcohol solution of the compound.

d. Reaction of an $N^2$-naphthalenesulfonyl-L-arginyl halide and an amine

An $N^2$-naphthalenesulfonyl-L-argininamide is prepared by reaction of a corresponding $N^2$-naphthalenesulfonyl-L-arginyl halide and an amine. The $N^2$-naphthalenesulfonyl-L-arginyl halide is prepared by reacting a corresponding $N^2$-naphthalenesulfonyl-L-arginine with a halogenating agent such as thionyl chloride, phosphorus oxychloride, phosphorus trichloride, phosphorus pentachloride, phosphorus tribromide, etc.

Although the halogenation proceeds without solvent, an inert solvent such as chlorinated hydrocarbons, e.g., chloroform, dichloromethane, etc., ethers, e.g., tetrahydrofuran, dioxane, etc., may preferably be used.

Usually the halogenating agent is used at least in an equimolar amount to the $N^2$-naphthalenesulfonyl-L-arginine.

The amount of the solvent to be used is not critical. But it is suitable to use a solvent in an amount 5 – 100 times the weight of the $N^2$-naphthalenesulfonyl-L-arginine.

The preferred reaction temperature is in the range of from $-10°$ C to room temperature. The reaction time varies with the halogenating agent and reaction temperature, and usually is from 15 minutes to 5 hours.

Amidation proceeds without solvent, but the use of a solvent such as dimethylformamide, and halogenated solvent (chloroform, dichloromethane, etc.), gives better results. Usually the amine is used at least in an equimolar amount to the $N^2$-naphthalenesulfonyl-L-arginyl halide.

The amount of the solvent to be used is not critical, but is usually about 5 – 100 times by weight the amount of the $N^2$-naphthalenesulfonyl-L-arginyl halide.

The preferred reaction temperature is in the range of from $-10°$ C to room temperature. The reaction time depends on the species of the amine and usually is from 5 minutes to 10 hours.

e. Guanidylation of an $N^2$-naphthalenesulfonyl-L-ornithinamide or an acid addition salt thereof An $N^2$-naphthalenesulfonyl-L-argininamide or an acid addition salt thereof is prepared by guanidylating a corresponding $N^2$-naphthalenesulfonyl-L-ornithinamide or an acid addition salt thereof. The guanidylation is performed by using ordinary guanidylating agents such as an O-alkylisourea, and S-alkylisothiourea, 1-guanyl-3,5-dimethylpyrazole, carbodiimide, etc., and O-alkylisourea and S-alkylisothiourea are especially preferred guanidylating agents.

The reaction of the $N^2$-naphthalenesulfonyl-L-ornithinamide or its acid addition salt with an O-alkylisourea or an S-alkylisothiourea is carried out usually in the presence of a base. The bases to be used include organic bases such as triethylamine, pyridine, etc.; common inorganic bases such as sodium hydroxide, potassium hydroxide, potassium carbonate, etc. Inorganic bases are usually used in the form of an aqueous solution.

The base is used in an amount of 0.01 to 0.1 equivalent to the $N^2$-naphthalenesulfonyl-L-ornithinamide. When an acid addition salt of an $N^2$-napthalenesulfonyl-L-ornithinamide is used as the starting material, it is necessary to use a base in an amount sufficient to neutralize the acid addition salt.

The O-alkylisourea or S-alkylisothiourea is usually used in the equimolar amount.

Generally, the reaction of an $N^2$-naphthalenesulfonyl-L-ornithinamide or an acid addition salt thereof with an O-alkylisourea or an S-alkylisothiourea is conducted in a solvent.

The preferred solvents include: water; alcohols such as methanol, ethanol, propanol, etc.; ethers such as tetrahydrofuran, dioxane, tetrahydropyran, etc.; ketones such as acetone, methyl ethyl ketone, etc.; basic solvents such as dimethylacetamide, dimethylformamide, etc.; and mixtures of any two or more of them.

The reaction temperature varies with the $N^2$-naphthalenesulfonyl-L-ornithinamide and base, and usually is between 0° C and the boiling temperature of the solvent.

The reaction time varies with the $N^2$-naphthalenesulfonyl-L-ornithinamide, base, solvent and the employed reaction temperature, and usually is in the range of from 30 minutes to 50 hours.

After the reaction is completed, the solvent is distilled off and the excess base and the formed salt are removed by washing with water.

The $N^2$-naphthalenesulfonyl-L-argininamide is obtained by purifying the product by column chromatography with silica gel.

The thus obtained $N^2$-naphthalenesulfonyl-L-argininamide may be treated with ether and an acid such as hydrochloric acid, p-toluenesulfonic acid, etc. to isolate the acid addition salt of the $N^2$-naphthalenesulfonyl-L-argininamide.

$N^2$-naphthalenesulfonyl-L-arginine esters and amides of this invention having the formula (I) form acid addition salts with any of a variety of inorganic and organic acids. The product of the reactions described above can be isolated as the free base or as the acid addition salt. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzensulfonic, p-toluenesulfonic acid or the like.

As stated above, $N^2$-naphthalenesulfonyl-L-arginine esters and amides, and acid addition salts thereof of this invention are characterized by highly specific inhibitory activity against thrombin, and therefore these compounds are useful in the determination of thrombin in blood as diagnostic reagents, and/or for the medical control or prevention of thrombosis.

The anthithrombotic activities of the $N^2$-naphthalenesulfonyl-L-arginine derivatives of this invention were compared with those of a known antithrombotic agent, [$N^2$-(p-tolysulfonyl)-L-arginine methyl ester], by determining the fibrinogen coagulation time. The measurement of the fibrinogen coagulation time was conducted as follows:

An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath. Immediately after mixing, the reaction mixture was transferred from the ice bath to a bath maintained at 25° C. Coagulation times were taken as the period between the time of transference to the 25° C bath and the time of the first appearance of fibrin threads. In the cases where no drug samples were added, the coagulation time was 50 – 55 seconds.

The experimental results are summarized in Table 1. The term "concentration required to prolong the coagulation time by a factor of two" is the concentration of an active ingredient required to prolong the normal coagulation time 50 – 55 seconds to 100 – 110 seconds.

The concentration required to prolong the coagulation time by a factor of two for the known antithrombotic agent, $N^2$-(p-tolysuofonyl)-L-arginine methyl ester, was 1100 μM.

The inhibitors are shown in Table 1 by indicating R and R' in the general formula (II) and the added acid.

When a solution containing an $N^2$-naphthalenesulfonyl-L-arginine derivative of this invention was administered intravenously into animal bodies, the high antithrombotic activity in the circulating blood was maintained for from one to three hours. The halflife for decay of the antithrombotic compounds of this invention in circulating blood was shown to be approximately 30 minutes; the physiological conditions of the host animals (rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined 24 hours after oral administration of substances of formula (I) in mice (male, 20 g) range from about 1,000 to 10,000 milligrams per kilogram of body weight. Representative $LD_{50}$ values, for example, for 4-[$N^2$-(5,6,7,8-tetrahydro-2-naphthalenesulfonyl)-L-arginyl]morpholine, 4-methyl-1-[$N^2$-(7-methoxy-2-naphthalenesulfonyl)-L-arginyl)]piperidine, and 4-methoxy-1[$N^2$-(7-methoxy-2-naphthalenesulfonyl)-L-arginyl]piperidine are 3000, 3000, >3000 milligrams per kilogram, respectively.

The therapeutic agents in this invention may be administered along or in combination with pharmaceutically acceptable carriers, the proportion of which is determined by the solubility and chemical nature of the compound, chosen route of administration and standard pharmaceutical practice. For example, the compounds may be injected parenterally, that is, intramuscularly, intravenously or subcutaneously. For parenteral administration, the compounds may be used in the form of sterile solutions containing other solutes, for examples, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents.

Physicians will determine the dosage of the present therapeutic agents which will be most suitable, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally. The therapeutic dosage is generally 10 – 50 mg/kg of active ingredient parenterally, 10 – 500 mg/kg orally per day.

Having generally described the invention, a more complete understanding of the synthetic processes for the compounds of this invention can be obtained by reference to the following specific examples, which are included for purposes of illustration only and are not intended to be limiting unless otherwise specified.

EXAMPLE 1

To an ice-cooled suspension of 1.0 gram of $N^2$-(2-naphthalenesulfonyl)-L-arginine in 15 ml of methanol was added dropwise 0.5 ml of thionyl chloride with vigorous stirring. After being allowed to stand for 2 hours at room temperature, the reaction mixture was refluxed for 2 hours, and was evaporated to dryness (syrup). Treatment of the residual syrup with cold ethyl ether gave crude crystals. After recrystallization from methanol-ethyl ether, colorless $N^2$-(2-naphthalenesulfonyl)-L-arginine methyl ester hydrochloride was obtained in 90% yield; mp. 183° – 186° C.

| Elemental analysis (as $C_{17}H_{22}O_4N_4S \cdot HCl$) | | | |
|---|---|---|---|
| | C | H | N |
| Calculated: | 49.21 | 5.59 | 13.50 |
| Found: | 49.35 | 5.61 | 13.21 |

EXAMPLE 2

A 3.0 gram amount of 4-[$N^G$-nitro-$N^2$-(5,6,7,8-tetrahydro-2-naphthalenesulfonyl)-L-arginyl]morpholine was dissolved in 50 ml of ethanol and 5 ml of acetic acid. A 0.5 g amount of palladium-black was added and the mixture was shaken in a stream of hydrogen for 100 hours at room temperature. After filtering off the catalyst, the filtrate was evaporated to give a viscous oily product. Reprecipitation from methanolethyl ether gave 4-[$N^2$-(5,6,7,8-tetrahydro-2-naphthalenesulfonyl)-L-arginyl]morpholine acetate in a powder form in 73% yield.

| Elemental analysis (as $C_{20}H_{31}O_4N_5S \cdot CH_3COOH$) | | | |
|---|---|---|---|
| | C | H | N |
| Calculated: | 53.10 | 7.09 | 14.08 |
| Found: | 53.28 | 7.09 | 14.00 |

EXAMPLE 3

A 1.0 gram amount of 4-ethyl-1-[$N^G,N^G$-dibenzyloxycarbonyl-$N^2$-(5,6,7,8-tetrahydro-1-naphthalenesulfonyl)-1-arginyl]piperidine was dissolved in a mixture of 50 ml of ethanol and 5 ml of acetic acid. An 0.5 amount of palladium-black was added to the mixture, which was then shaken in a stream of hydrogen for 10 hours at room temperature. After filtering off the catalyst, the filtrate was evaporated to give a viscous oil product. Reprecipitation from ethanolethyl ether gave 4-ethyl-1-[$N^2$-(5,6,7,8-tetrahydro-1-naphthalenesulfonyl)-L-arginyl]piperidine acetate in a powder form in 74% yield.

| Elemental analysis (as $C_{23}H_{37}O_3N_5S \cdot CH_3COOH$) | | |
|---|---|---|
| C | H | N |
| Calculated: 57.33 | 7.89 | 13.37 |
| Found: 56.98 | 7.89 | 13.28 |

EXAMPLE 4

A 1.0 gram amount of 4-methyl-1-[$N^G$-nitro-$N^2$-(5,6,7,8-tetrahydro-1-naphthalenesulfonyl)-L-arginyl]piperidine was dissolved in a mixture of 0.44 g of anisole and 10 ml of hydrogen fluoride, and the mixture was stirred for 30 minutes in an ice-bath. The hydrogen fluoride was evaporated in vacuo to afford an oily products, which was washed well with 100 ml of dry ethyl ether to remove the hydrogen fluoride. Reprecipitation from methanol-ethyl ether gave 4-methyl-1-[$N^2$-(5,6,7,8-tetrahydro-1-naphthalenesulfonyl)-L-arginyl]piperidine hydrofluoride in a powder form in 78% yield.

| Elemental analysis (as $C_{22}H_{35}O_3N_5S \cdot HF$) | | |
|---|---|---|
| C | H | N |
| Calculated: 56.26 | 7.73 | 14.91 |
| Found: 55.89 | 7.70 | 14.90 |

EXAMPLE 5

To a solution of 1.00 gram of 4-($N^2$-1-naphthalenesulfonyl-L-ornithyl)morpholine in 30 ml of 30% aqueous methanol was added 1.30 ml of 2N NaOH and 0.25 gram of 0-methylisourea hydrochloride. After having being stirred for 15 hours at 40° C, the reaction mixture was evaporated to dryness. The residual material was extracted with 40 ml of chloroform and washed with 10 ml of water. The chloroform layer was dried over anhydrous $CaCl_2$. After removal of the solvent, the residue was redissolved in 20 ml of chloroform, and adsorbed into 50 g of Wakogel C-200 which was packed in a 50 cm × 3 cm column. The column was eluted with chloroform-methanol (V/V=9/1).

After the solvent removal under reduced pressure, the residue was dissolved in 30 ml of chloroform-acetic acid (V/V=19/1). The addition of dry ethyl ether produces an oily deposit, which was washed several times with dry ethyl ether. The obtained solid substances, 4-[$N^2$-(1-naphthalenesulfonyl)-L-arginyl]morpholine, was finely pulverized, collected, and dried in vacuo over phosphorus pentoxide, in 23% yield.

| Elemental analysis (as $C_{20}H_{27}N_5O_4S \cdot CH_3COOH$) | | |
|---|---|---|
| C | H | N |
| Calculated: 53.54 | 6.33 | 14.19 |
| Found: 53.21 | 6.31 | 14.11 |

EXAMPLE 6

A 1.0 gram amount of $N^2$-(1-naphthalenesulfonyl)-L-arginine methyl ester hydrochloride was dissolved in 2 ml of methoxyethylamine with vigorous agitation. After the resulting solution was allowed to stand at room temperature for 2 days, the methoxyethylamine was removed in vacuo and the residual syrup was washed well with 5 ml of water to obtain a powdery product. And then this powder was dissolved in minimum volume of acetic acid. To this solution ethyl ether was added to precipitate the viscous oily product. Reprecipitation from ethanol-ethyl ether gave $N^2$-(1-naphthalenesulfonyl)-N-butyl-L-argininamide acetate in a powder form in 77% yield.

| Elemental analysis (as $C_{19}H_{27}O_4N_5S \cdot C_2H_4O_2$) | | |
|---|---|---|
| C | H | N |
| Calculated: 52.37 | 6.49 | 14.54 |
| Found: 52.18 | 6.21 | 14.50 |

EXAMPLE 7

To a mixture of 1.0 gram of 4-ethyl-1-(L-arginyl)-piperidine and 0.61 gram $K_2CO_3$ in 10 ml of water was added dropwise a solution of 1.0 grams of 1-naphthalenesulfonyl chloride in 30 ml of dioxane with vigorous stirring for a period of over 30 minutes while maintaining the temperature at 0° C. The reaction mixture was stirred for an additional 5 hours and the formed precipitate was removed by filtration. The solvent was evaporated, and to the residue was added 50 ml of $CHCl_3$. A small amount of the undissolved material was filtered and the solution was dried over anhydrous $Na_2SO_4$. To the stirred solution was added 20 ml of ether containing 0.5 gram of acetic acid to precipitate 4-ethyl-1-[$N^2$-(1-naphthalenesulfonyl)-L-arginyl]piperidine acetate, which was purified by reprecipitation from a methanol-ethyl ether mixture in 70% yield.

| Elemental analysis (as $C_{23}H_{33}O_3N_5S \cdot CH_3COOH$) | | |
|---|---|---|
| C | H | N |
| Calculated: 57.59 | 7.15 | 14.60 |
| Found: 57.37 | 7.28 | 14.69 |

EXAMPLE 8

A mixture of 1.0 gram of $N^2$-(5-nitro-1-naphthalenesulfonyl)-L-arginine, 1.0 gram of p-toluenesulfonic acid monohydrate in 5 ml of n-butyl alcohol and 30 ml of benzene was refluxed for 5 hours, removing water by azeotropic distillation. After the solvent was removed by distillation, 100 ml of ethyl ether was added to the residue, giving a crystalline mass of $N^2$-(5-nitro-1-naphthalenesulfonyl)-L-arginine butyl ester p-toluenesulfonate in 95% yield; mp. 94° – 95° C.

| Elemental analysis (as $C_{20}H_{27}O_6N_5S \cdot C_7H_8O_3S$) | | |
|---|---|---|
| C | H | N |
| Calculated: 50.95 | 5.53 | 10.98 |

-continued
| Elemental analysis (as $C_{20}H_{27}O_6N_5S \cdot C_7H_8O_3S$) | | |
|---|---|---|
| C | H | N |
| Found: 50.86 | 5.63 | 10.02 |
| No. | R | R' | Addition moiety | Preparation process (Ex. No.) | Property or m.p. (°C) | Elemental analysis Upper: Calculated Lower: Found | | | Concentration required to prolong the coagulation time by a factor of two (μM) |
|---|---|---|---|---|---|---|---|---|---|
| | | | | | | C | H | N | |
| 1 | 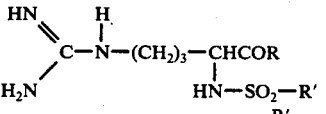 | 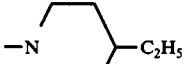 | HF | 4 | " | 57.59 57.37 | 7.15 7.28 | 14.60 14.69 | 1.0 |
| 2 | 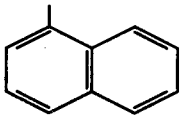 | " | CH₃COOH | 7 | " | 57.01 56.92 | 6.98 6.79 | 13.85 14.01 | 4.0 |
| 3 | 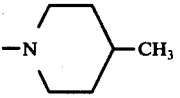 | " | " | 2 | " | 57.01 56.89 | 6.98 6.69 | 13.85 14.00 | 10 |
| 4 |  | " | " | 5 | " | 53.54 53.21 | 6.33 6.31 | 14.19 14.11 | 20 |
| 5 | 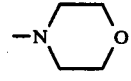 | " | HF | 4 | " | 59.36 59.20 | 5.81 5.59 | 14.42 14.71 | |
| 6 | 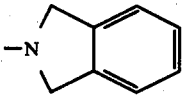 | 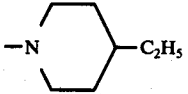 | HF | 4 | Powder | 57.59 57.39 | 7.15 7.00 | 14.60 14.89 | 1.0 |
| 7 | 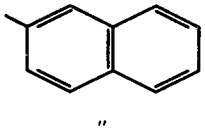 | " | CH₃COOH | 7 | " | 57.01 56.81 | 6.98 6.81 | 13.85 13.99 | 4.5 |
| 8 | 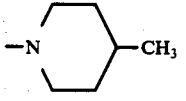 | " | " | 7 | " | 57.01 56.71 | 6.98 6.71 | 13.85 14.02 | 20 |
| 9 |  | " | " | 2 | " | 56.63 53.29 | 6.33 6.31 | 14.19 14.02 | 20 |
| 10 | 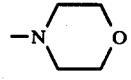 | " | HF | 4 | " | 55.61 55.61 | 7.11 7.29 | 15.44 15.80 | 50 |
| 11 |  | 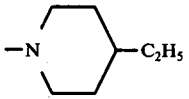 | HF | 4 | " | 57.12 56.82 | 6.59 6.29 | 16.60 16.26 | 6.0 |

-continued

| No. | R | R' | Addition moiety | Preparation process (Ex. No.) | Property or m.p. (°C) | Elemental analysis Upper: Calculated Lower: Found C / H / N | Concentration required to prolong the coagulation time by a factor of two (μM) |
|---|---|---|---|---|---|---|---|

Structural formula at top:

$$\begin{array}{c} HN \\ \phantom{HN}\diagdown \\ \phantom{HN}C-N-(CH_2)_3-CHCOR \\ H_2N\diagup \phantom{C-N} | \phantom{(CH_2)_3-CH}| \\ \phantom{H_2N\diagup C-N}H \phantom{(CH_2)_3-CH}HN-SO_2-R' \end{array}$$

| No. | R | R' | Addition moiety | Prep. (Ex. No.) | m.p. (°C) | C | H | N | μM |
|---|---|---|---|---|---|---|---|---|---|
| 12 | −N⟨piperidine-4-C₂H₅⟩ | 6-methyl-2-naphthyl | CH₃COOH | 2 | " | 58.51 / 58.21 | 7.37 / 7.17 | 13.12 / 13.51 | 0.5 |
| 13 | " | 5-chloro-1-methyl-naphthyl | " | 7 | " | 54.19 / 53.89 | 6.55 / 6.51 | 12.64 / 12.73 | 2.0 |
| 14 | " | 7-methyl-1-methyl-naphthyl | " | 7 | " | 58.51 / 58.43 | 7.37 / 7.09 | 13.12 / 13.42 | 1.0 |
| 15 | " | 6,7-dimethyl-naphthyl | " | 2 | " | 58.51 / 58.29 | 7.37 / 7.36 | 13.12 / 13.07 | 0.4 |
| 16 | " | 5-nitro-1-methyl-naphthyl | HF | 4 | " | 52.65 / 52.29 | 6.34 / 6.20 | 16.02 / 16.31 | 1.0 |
| 17 | " | 6-ethyl-2-methyl-naphthyl | CH₃COOH | 2 | " | 59.21 / 59.00 | 7.55 / 7.31 | 12.79 / 12.48 | 0.7 |
| 18 | " | 6-isopropyl-2-methyl-naphthyl | " | 7 | " | 59.87 / 59.70 | 7.72 / 7.71 | 12.47 / 12.40 | |
| 19 | −N(H)(CH₂CH₂OCH₃) | 1-methyl-naphthyl | " | 6 | " | 52.37 / 52.18 | 6.49 / 6.21 | 14.54 / 14.50 | |
| 20 | −N(H)(CH₂CH₂CH₂CH₃) | " | " | 6 | " | 55.09 / 54.00 | 6.94 / 6.78 | 14.60 / 14.41 | 5.0 |
| 21 | −N(CH₃)(CH₂CH₂COOCH₃) | 7-methyl-2-methyl-naphthyl | " | 7 | " | 53.61 / 53.54 | 6.56 / 6.28 | 13.03 / 13.28 | |

-continued
| No. | R | R' | Addition moiety | Preparation process (Ex. No.) | Property or m.p. (° C) | Elemental analysis Upper: Calculated Lower: Found C | H | N | Concentration required to prolong the coagulation time by a factor of two (μM) |
|---|---|---|---|---|---|---|---|---|---|
| | 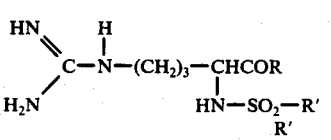 | | | | | | | | |
| 22 | 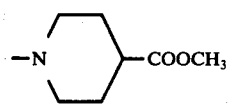 | " | " | 2 | " | 55.40 55.21 | 6.62 6.43 | 12.43 12.28 | |
| 23 | 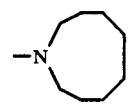 | " | " | 7 | " | 59.21 59.10 | 7.55 7.38 | 12.79 12.66 | |
| 24 | 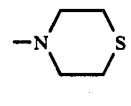 | 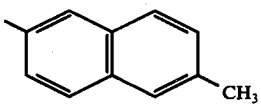 | HF | 4 | " | 52.15 51.98 | 6.25 6.20 | 14.48 14.29 | |
| 25 | 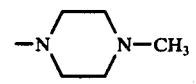 | " | 2CH₃COOH | 2 | " | 53.77 53.89 | 6.94 6.71 | 14.47 14.29 | |
| 26 | 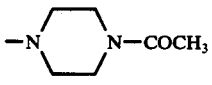 | " | CH₃COOH | 2 | " | 54.73 54.51 | 6.61 6.41 | 15.32 15.09 | |
| 27 | 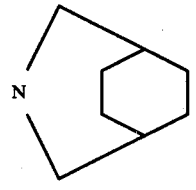 | 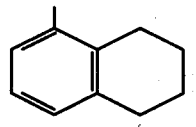 | " | 2 | " | 58.73 58.43 | 7.01 7.21 | 13.17 13.00 | 16 |
| 28 | 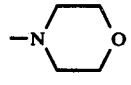 | 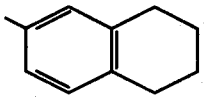 | " | 2 | " | 53.10 53.28 | 7.09 7.09 | 14.08 14.00 | 7.5 |
| 29 | 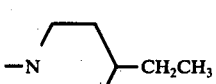 | 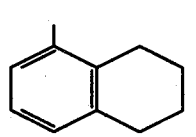 | " | 3 | " | 57.33 56.98 | 7.89 7.89 | 13.37 13.28 | 0.5 |
| 30 | 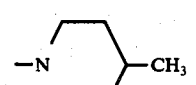 | " | HF | 4 | " | 56.26 55.89 | 7.73 7.70 | 14.91 14.90 | 1.0 |
| 31 | 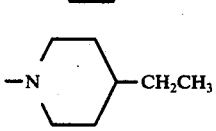 | 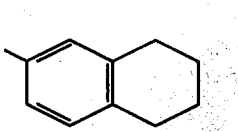 | HF | 4 | " | 57.11 56.89 | 7.92 7.89 | 14.48 14.25 | 0.7 |
| 32 | 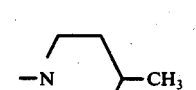 | " | CH₃COOH | 2 | " | 56.56 56.89 | 7.71 7.69 | 13.74 13.54 | 0.6 |
| 33 | 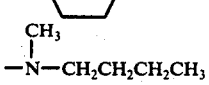 | 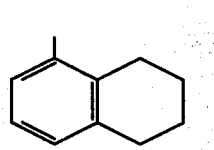 | HF | 4 | " | 55.12 55.03 | 7.93 7.92 | 15.31 15.28 | 50 |

-continued

Structural formula for the series:

$$\begin{array}{c} HN \\ \phantom{x} \backslash \\ \phantom{xx} C-N-(CH_2)_3-CHCOR \\ H_2N\phantom{xxx}|\phantom{xxxxxxx}| \\ \phantom{xxxxxxxxxxxx}HN-SO_2-R' \end{array}$$

| No. | R | R' | Addition moiety | Preparation process (Ex. No.) | Property or m.p. (°C) | Elemental analysis Upper: Calculated Lower: Found C / H / N | Concentration required to prolong the coagulation time by a factor of two (μM) |
|---|---|---|---|---|---|---|---|
| 34 | −N(CH₃)−CH₂−C₆H₅ | " | " | 4 | " | 58.63 6.97 14.25 / 58.43 6.59 14.00 | 20 |
| 35 | −NH−CH₂CH₂CH₂CH₃ | 5,6,7,8-tetrahydronaphthalen-2-yl | " | 4 | " | 54.15 7.73 15.79 / 54.11 7.72 15.61 | 5 |
| 36 | −NH−CH₂CH₂OCH₃ | 5,6,7,8-tetrahydronaphthalen-2-yl | CH₃COOH | 2 | " | 51.94 7.27 14.42 / 51.83 7.25 14.29 | |
| 37 | −NH−CH₂CH₂COOCH₃ | 5,6,7,8-tetrahydronaphthalen-2-yl | " | 2 | " | 51.44 6.87 13.64 / 51.28 6.77 13.51 | |
| 38 | −N(piperazinyl)−N−CH₃ | 5,6,7,8-tetrahydronaphthalen-2-yl | 2HF | 4 | Powder | 51.40 7.40 17.13 / 50.98 7.35 17.03 | |
| 39 | −N(piperidinyl)−COOCH₃ | 5,6,7,8-tetrahydronaphthalen-2-yl | CH₃COOH | 2 | " | 54.23 7.10 12.65 / 54.21 7.00 12.31 | |
| 40 | −N(azocanyl) | 5,6,7,8-tetrahydronaphthalen-2-yl | HF | 4 | " | 57.11 7.92 14.48 / 57.08 7.82 14.39 | |
| 41 | −N(piperidinyl)−C(=O)CH₃ | 5,6,7,8-tetrahydronaphthalen-2-yl | " | 4 | " | 55.50 7.29 14.07 / 55.31 7.29 14.11 | |
| 42 | −N(tetrahydroisoquinolinyl) | 5,6,7,8-tetrahydronaphthalen-2-yl | " | 4 | " | 58.87 6.59 14.31 / 58.71 6.48 14.31 | |
| 43 | −NH−CH₂−cyclohexyl | 5,6,7,8-tetrahydronaphthalen-2-yl | CH₃COOH | 2 | " | 57.33 7.89 13.37 / 57.20 7.88 13.28 | |
| 44 | −N(piperidinyl)−OCH₃ | 5,6,7,8-tetrahydronaphthalen-2-yl | CH₃COOH | 2 | Powder | 54.83 7.48 13.32 / 54.59 7.48 13.08 | |
| 45 | −N(thiomorpholinyl) | 5,6,7,8-tetrahydronaphthalen-2-yl | " | 2 | " | 51.44 6.87 13.64 / 51.09 6.87 13.61 | |
| 46 | −N(piperazinyl)−N−C(=O)OCH₃ | 5,6,7,8-tetrahydronaphthalen-2-yl | " | 2 | " | 53.51 7.11 15.60 / 53.43 7.10 15.55 | |

-continued

| No. | R | R' | Addition moiety | Preparation process (Ex. No.) | Property or m.p. (° C) | Elemental analysis Upper: Calculated Lower: Found C | H | N | Concentration required to prolong the coagulation time by a factor of two (μM) |
|---|---|---|---|---|---|---|---|---|---|
| 47 | —OCH₃ | 1-methylnaphthyl | HCl | 1 | " | 49.21 / 49.10 | 5.59 / 5.61 | 13.50 / 13.34 | 520 |
| 48 | —OCH₃ | 6-methyl-2-naphthyl | " | 1 | 183–186 | 49.21 / 49.35 | 5.59 / 5.61 | 13.50 / 13.21 | 130 |
| 49 | —O—n-C₄H₉ | 5-methyl-4-nitro-1-naphthyl | " | 8 | 94–95 | 50.95 / 50.86 | 5.53 / 5.63 | 10.98 / 11.02 | 35 |
| 50 | —O—n-C₃H₇ | 5-methyl-4-nitro-1-naphthyl | p-toluene-sulfonic acid | 8 | 90–93 | 50.07 / 50.13 | 5.33 / 5.35 | 11.23 / 11.29 | 50 |
| 51 | —O—n-C₄H₉ | 6-methyl-2-ethyl-naphthyl | " | 8 | 127–130 | 56.10 / 56.00 | 6.49 / 6.39 | 9.03 / 9.12 | 2.5 |
| 52 | —O-cyclohexyl | " | " | 8 | Powder | 57.76 / 57.49 | 6.54 / 6.61 | 8.66 / 8.71 | |
| 53 | —OCH₂CH=CHCH₃ | " | " | 8 | 118–120 | 56.29 / 56.30 | 6.14 / 6.08 | 9.05 / 9.02 | |
| 54 | —O—n-C₄H₉ | 5-methyl-8-chloro-1-naphthyl | " | 8 | Powder | 51.70 / 51.66 | 5.62 / 5.59 | 8.94 / 8.93 | 4.0 |

What is claimed as new and intended to be covered by Letters patent is:

1. N²-naphthalenesulfonyl-L-arginine amides having the formula

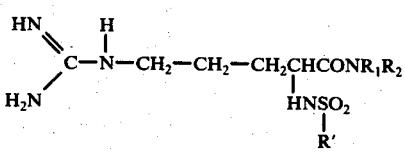

or the acid addition salts thereof with a pharmaceutically acceptable acid, wherein R₁ and R₂ are members selected from the group consisting of hydrogen and a hydrocarbon selected from the group consisting of alkyl, aryl, cycloalkyl, respectively containing not more than 10 carbon atoms, and aralkyl and cycloalkylalkyl, respectively containing not more than 15 carbon atoms, or R₁ and R₂ together are polymethyleneiminyl of 3-10 carbon atoms, optionally substituted by 1 or 2 alkyl groups containing not more than 10 carbon atoms; and R' is a member selected from the class consisting of 5, 6, 7, 8-tetrahydro-1-naphthyl, 5,6,7,8-tetrahydro-2-naphthyl, 1-naphthyl, 2-naphthyl, 1-naphthyl substituted with one member selected from the class consisting of halogen, nitro, cyano, hydroxy, alkyl containing not more than 10 carbon atoms, 2-naphthyl substituted with one member selected from the class consisting of halogen, nitro, cyano, hydroxy and alkyl containing not more than 10 carbon atoms.

2. The compounds of claim 1 wherein R₁ is hydrogen and R₂ is a member selected from the class consisting of alkyl, aryl, and cycloalkyl, respectively containing not more than 10 carbon atoms, and aralkyl and cycloalkylalkyl, respectively containing not more than 15 carbon atoms and R' is a member selected from the class consisting of 5,6,7,8-tetrahydro-1-naphthyl, 5,6,7,8-tetrahydro-2-naphthyl, 1-naphthyl, 2-naphthyl, 1-naphthyl substituted with one member selected from the class consisting of halogen, nitro, cyano, hydroxy, alkyl containing not more than 10 carbon atoms, 2-naphthyl substituted with one member selected from the class consisting of halogen, nitro, cyano, hydroxy, alkyl containing not more than 10 carbon atoms.

3. The compounds of claim 2, wherein the entity is a member

selected from the class consisting of alkylamino of 1-9 carbon atoms, cycloalkylamino of 3-6 carbon atoms, arylamino of 6-10 carbon atoms, and aralkylamino and cycloalkylalkylamino, respectively of 7-10 carbon atoms, and R' is a member selected from the class consisting of 5,6,7,8-tetrahydro-1-naphthyl, 5,6,7,8-tetrahydro-2-naphthyl, 1-naphthyl, 2-naphthyl, 1-naphthyl substituted with one member selected from the class consisting of halogen, nitro, cyano, hydroxy, alkyl containing not more than 5 carbon atoms, and 2-naphthyl substituted with one member selected from the class consisting of halogen, nitro, cyano, hydroxy, alkyl containing not more than 5 carbon atoms.

4. The compounds of claim 3, the entity

is a member selected from the class consisting of butylamino, cyclohexylmethylamino and benzylamino, and R' is a member selected from the class consisting of 5,6,7,8-tetrahydro-1-naphthyl, 5,6,7,8-tetrahydro-2-naphthyl, 1-naphthyl, 2-naphthyl, 5-chloro-1-naphthyl, 5-nitro-1-naphthyl, 5-cyano-1-naphthyl, 5-hydroxy-1-naphthyl, 7-methyl-1-naphthyl, 7-methyl-2-naphthyl, 6-methyl-2-naphthyl, 6-ethyl-2-naphthyl, 6-propyl-2-naphthyl.

5. The compounds of claim 1, wherein $R_1$ and $R_2$ are repectively a member selected from the class consisting of alkyl and aryl, respectively containing not more than 10 carbon atoms, and aralkyl and cycloalkylakyl, respectively containing not more than 15 carbon atoms and R' is a member selected from the class consisting of 5,6,7,8-tetrahydro-1-naphthyl, 5,6,7,8-tetrahydro-2-naphthyl, 1-naphthyl, 2-naphthyl, 1-naphthyl substituted with one member selected from the class consisting of halogen, nitro, cyano, hydroxy, alkyl containing not more than 10 carbon atoms, 2-naphthyl substituted with one member selected from the class consisting of halogen, nitro, cyano, hydroxy, alkyl containing not more than 10 carbon atoms.

6. The compounds of claim 5 wherein the entity,

is a member selected from the class consisting of dialkylamino of 2-10 carbon atoms, and N-alkyl-N-aralkylamino of 8-10 carbon atoms; and R' is a group selected from the class consisting of 5,6,7,8-tetrahydro-1-naphthyl, 5,6,7,8-tetrahydro-2-naphthyl, 1-naphthyl, 2-naphthyl, 1-naphthyl substituted with one member selected from the class consisting of halogen, nitro, cyano, hydroxy, alkyl containing not more than 5 carbon atoms, and 2-naphthyl substituted with one member selected from the class consisting of halogen, nitro, cyano, hydroxy, alkyl containing not more than 5 carbon atoms.

7. The compounds of claim 6, wherein the entity,

is a member selected from the class consisting of N-methyl-N-butylamino, and N-methyl-N-benzylamino; and R' is a member selected from the class consisting of 5,6,7,8-tetrahydro-1-naphthyl, 5,6,7,8-tetrahydro-2-naphthyl, 1-naphthyl, 2-naphthyl, 5-chloro-1-naphthyl, 5-nitro-1-naphthyl, 5-cyano-1-naphthyl, 5-hydroxy-1-naphthyl, 7-methyl-1-naphthyl, 7-methyl-2-naphthyl, 6-methyl-2-naphthyl, 6-ethyl-2-naphthyl, 8. The compounds of claim 1, wherein $R_1$ and $R_2$ together are polymethyleneiminyl of 3-10 carbon atoms, optionally substituted by 1 or 2 alkyl groups of not more than 10 carbon atoms.

9. The compounds of claim 8, wherein the entity

is a member selected from the class consisting of N,N-polymethyleniminyl of 3-10 carbon atoms and N,N-polymethyleniminyl of 3-10 carbon atoms substituted with alkyl of 1-5 carbon atom of 2-5 carbon atoms, acyl of 2-5 carbon atoms, and carbamoyl; tetrahydro-l,n-oxazin-yl, wherein n is an integer of 2, 3 or 4; tetrahydro-l,thiazin-n-yl, wherein n is an integer of 2, 3 or 4; 2-isoindolinyl; 1-piperazinyl substituted with alkyl of 1-5 carbon atoms or acyl of 2-5 carbon atoms; and 4-azabicyclo; and R' is a group selected from the class consisting of 5,6,7,8-tetrahydro-1-naphthyl, 5,6,7,8-tetrahydro-2-naphthyl, 1-naphthyl, 2-naphthyl, 1-naphthyl substituted with one member selected from the class consisting of halogen, nitro; cyano, hydroxy, alkyl containing not more than 5 carbon atoms, and 2-naphthyl substituted with one member selected from the class consisting of halogen, nitro, cyano, hydroxy, and alkyl containing not more than 5 carbon atoms.

10. The compounds of claim 9, wherein the entity

is a member selected from the class consisting of piperidino, hexamethyleniminyl, heptamethyleniminyl, octamethyleniminyl, 4-methylpiperidino, and 4-ethylpiperidino; and R' is a member selected from the class consisting of 5,6,7,8-tetrahydro-1-naphthyl, 5,6,7,8-tetrahydro-2-naphthyl, 1-naphthyl, 2-naphthyl, 5-chloro-1-naphthyl, 5-nitro-1-naphthyl, 5-cyano-1-naphthyl, 5-hydroxy-1-naphthyl, 7-methyl-1-naphthyl, 7-methyl-2-naphthyl, 6-methyl-2-naphthyl, 6-ethyl-2-naphthyl, 6-propyl-2-naphthyl.

* * * * *

UNITED STATES PATENT AND TRADEMARK OFFICE
CERTIFICATE OF CORRECTION

PATENT NO. : 4,049,645

DATED : September 20, 1977

INVENTOR(S) : SHOSUKE OKAMOTO ET AL

It is certified that error appears in the above-identified patent and that said Letters Patent are hereby corrected as shown below:

In the abstract, line 3, that portion of the formula reading $$\begin{array}{c}-CHCOR\\|\\HNSO_2\\|\\R'\end{array} \quad \text{should appear as follows:} \quad \begin{array}{c}-CHCOR\\|\\HNSO_2\\|\\R'\end{array}$$

In the abstract, line 10, delete "aralykyl", and insert --aralkyl--;

In the abstract, line 11, after "atoms", insert --, or $R_1$ and $R_2$ together are polymethyleneiminyl of 3-10 carbon atoms, optionally substituted by 1 or 2 alkyl groups containing not more than 10 carbon atoms--;

In the abstract, line 17, delete "ot", and insert --not--;

Column 1, line 21, delete "p-tolysulfonyl", and insert --p-tolylsulfonyl

Column 1, line 24, delete "dansyl-1-", and insert --dansyl-L---;

Column 1, line 26, delete "continue", and insert --continues--;

UNITED STATES PATENT AND TRADEMARK OFFICE
CERTIFICATE OF CORRECTION

PATENT NO. : 4,049,645
DATED : September 20, 1977
INVENTOR(S) : SHOSUKE OKAMOTO ET AL It is certified that error appears in the above—identified patent and that said Letters Patent are hereby corrected as shown below:

Column 1, line 27, delete "on", and insert --of--;

Column 1, line 32, delete "-naphthalenesulfony-", and insert -- -naphthalenesulfonyl- --;

Column 1, line 45, delete "(l)", and insert --(I)--;

Column 1, line 54, delete "(I)", and insert --(l)--;

Column 2, line 6, delete "arylcarbom-", and insert --arylcarbam---;

Column 3, line 3, the formula reading -N Z should appear as -N⟩ ;

Column 3, line 24, delete "tertbutoxy", and insert --tert-butoxy--;

Column 3, line 44, delete "indepently", and insert --independently--;

Column 3, line 65, delete "2methoxycarbonylethyl", and insert --2-methoxycarbonylethyl--;

Column 4, line 32, delete "-tetrahydro-lor", and insert -- -tetrahydro-1- or --;

UNITED STATES PATENT AND TRADEMARK OFFICE
CERTIFICATE OF CORRECTION

PATENT NO. : 4,049,645

DATED : September 20, 1977

INVENTOR(S) : SHOSUKE OKAMOTO ET AL

Page 3 of 8

It is certified that error appears in the above-identified patent and that said Letters Patent are hereby corrected as shown below:

Column 4, line 52, delte "ω-acylakyl", and insert --ω-acylalkyl--;

Column 4, lines 57-58 delete "tetrahydro-1-,n-oxazin-n-yl", and insert --tetrahydro-1,n-oxazin-n-yl--;

Column 4, line 64, delete "4-arkyl-1-piperzinyl", and insert --4-alkyl-1-piperazinyl--;

Column 5, line 27, delete "melthyl", and insert --methyl--;

Column 5, line 39, delete "piperdine", and insert --piperidine--;

Column 5, line 41, delete "4-ethyl-1", and insert --4-ethyl-1- --;

Column 5, line 42, delete "piperedine", and insert --piperidine--;

Column 5, line 44, delete "piperdine", and insert --piperidine--;

Column 5, line 46, delete "$N^2$-8", and insert --$N^2$-(--;

Column 5, lines 47-78, delete "4-methoxyl-", and insert --4-methoxy-1--

Column 5, line 49, delete "4-methoxycarbonyl-1", and insert --4-methoxycarbonyl-1- --;

UNITED STATES PATENT AND TRADEMARK OFFICE
CERTIFICATE OF CORRECTION

PATENT NO. : 4,049,645

DATED : September 20, 1977

INVENTOR(S) : SHOSUKE OKAMOTO ET AL

It is certified that error appears in the above-identified patent and that said Letters Patent are hereby corrected as shown below:

Column 5, line 51, delete "tetrahydro-1", and insert --tetrahydro-1---;

Column 5, line 65, delete "Esterfication", and insert --Esterification-- delete "-1-arginine", and insert ---L-arginine --;

Column 6, line 25, delete "temperatues", and insert --temperatures--;

Column 6, line 33, delete "benzenessulfonic", and insert --benzenesulfonic--;

Column 6, line 42, delete "add", and insert --adds--;

Column 6, line 44, delete "esterfication", and insert --esterification--

Column 6, lines 46-47, delete "esterfication", and insert --esterification--;

Column 6, lines 50-51, delete "aralykyl", and insert --aralkyl--;

Column 7, line 25, delete "lequivalent", and insert --1 equivalent--;

Column 7, line 55, delete "(iV)", and insert --(iv)--;

UNITED STATES PATENT AND TRADEMARK OFFICE
CERTIFICATE OF CORRECTION

PATENT NO. : 4,049,645

DATED : September 20, 1977

INVENTOR(S) : SHOSUKE OKAMOTO ET AL

It is certified that error appears in the above-identified patent and that said Letters Patent are hereby corrected as shown below:

Column 8, line 17, delete "has", and insert --have--;

Column 8, lines 40-41, delete "solvent" (second occurrence), and insert --solvents--;

Column 9, line 13, delete "hexlamine", and insert --hexylamine--;

Column 9, line 16, delete "cycloalklamine", and insert --cycloalkylamine--;

Column 9, line 22, delete "2-methoxy, ethylamine", and insert --2-methoxyethylamine--;

Column 10, line 56, delete "purrolidone", and insert --pyrrolidone--;

Column 11, line 12, that portion of the formula reading 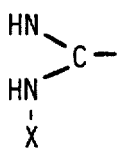 should appear as follows:

UNITED STATES PATENT AND TRADEMARK OFFICE
CERTIFICATE OF CORRECTION

PATENT NO. : 4,049,645            Page 6 of 8
DATED : September 20, 1977
INVENTOR(S) : SHOSUKE OKAMOTO ET AL It is certified that error appears in the above-identified patent and that said Letters Patent are hereby corrected as shown below:

Column 11, line 28, delete "tertbutoxycarbonyl", and insert --tert-butoxycarbonyl--;

Column 12, line 20, delete "-naphthalenesuflonyl-", and insert -- -naphthalenesulfonyl- --; delete "bu", and insert --by--;

Column 12, line 59, delete "catalyst", and insert --catalysts--;

Column 15, line 3, delete "thromabosis", and insert --thrombosis--;

Column 15, line 7, delete "p-tolysulfonyl", and insert --p-tolylsulfonyl--;

Column 15, line 33, delete "p-tolysuofonyl", and insert --p-tolylsulfonyl--;

Column 15, line 57, delete "4-methoxy-1", and insert --4-methoxy-1- --;

Column 15, line 60, delete "in", and insert --of--;

Column 16, line 1, delete "examples", and insert --example--;

UNITED STATES PATENT AND TRADEMARK OFFICE
CERTIFICATE OF CORRECTION

PATENT NO. : 4,049,645
DATED : September 20, 1977
INVENTOR(S) : SHOSUKE OKAMOTO ET AL It is certified that error appears in the above-identified patent and that said Letters Patent are hereby corrected as shown below:

Column 16, line 60, delete "methanolethyl", and insert --methanol-ethyl--;

Column 17, line 12, delete "ethanolethyl", and insert --ethanol-ethyl--;

Column 17, lines 30-31, delete "products", and insert --product--;

Column 20, line 53, delete "56.63", and insert --53.63--;

Column 24, line 61, delete "56.89", and insert --56.38--;

Column 25, line 40, delete  and insert  ;

Column 28, line 12, delete "5.61", and insert --5.29--;

Column 28, line 37, delete "57.76", and insert --57.56--;

Column 29, lines 8-9, delete "is a member";

Column 29, line 15, before "selected", insert --is a member--;

UNITED STATES PATENT AND TRADEMARK OFFICE
CERTIFICATE OF CORRECTION

PATENT NO. : 4,049,645

DATED : September 20, 1977

INVENTOR(S) : SHOSUKE OKAMOTO ET AL

It is certified that error appears in the above-identified patent and that said Letters Patent are hereby corrected as shown below:

Column 29, line 28, after "claim 3,", insert --wherein--;

Column 30, lines 37-43, delete "atom of 2-5 carbon atoms, acyl of 2-5 carbon atoms, and carbamoyl; tetrahydro-1,n-oxazin-yl, wherein n is an integer of 2, 3 or 4; tetrahydro-1,thiazin-n-yl, wherein n is an integer of 2, 3 or 4, 2-isoindolinyl; 1-piperazinyl substituted with alkyl of 1-5 carbon atoms or acyl of 2-5 carbon atoms; and 4-azabicyclo", and insert --atoms--;

Signed and Sealed this

Nineteenth Day of September 1978

[SEAL]

Attest:

RUTH C. MASON
Attesting Officer

DONALD W. BANNER
Commissioner of Patents and Trademarks